United States Patent
Liphardt et al.

(10) Patent No.: US 10,247,611 B1
(45) Date of Patent: Apr. 2, 2019

(54) ENHANCED DETECTOR OPERATION MADE POSSIBLE BY APPLICATION OF A FUNCTIONAL PLURALITY OF GRATINGS AND COMBINATION DICHROIC BEAM SPLITTER-PRISMS

(71) Applicants: Martin M. Liphardt, Lincoln, NE (US); Ping He, Lincoln, NE (US); Duane E. Meyer, Lincoln, NE (US)

(72) Inventors: Martin M. Liphardt, Lincoln, NE (US); Ping He, Lincoln, NE (US); Duane E. Meyer, Lincoln, NE (US)

(73) Assignee: J.A. WOOLLAM CO., INC., Lincoln, NE (US)

( * ) Notice: Subject to any disclaimer, the term of this patent is extended or adjusted under 35 U.S.C. 154(b) by 67 days.

(21) Appl. No.: 14/757,280

(22) Filed: Dec. 14, 2015

Related U.S. Application Data

(60) Provisional application No. 62/124,428, filed on Dec. 18, 2014.

(51) Int. Cl.
| | |
|---|---|
| *G01J 4/04* | (2006.01) |
| *G01J 3/447* | (2006.01) |
| *G01J 3/10* | (2006.01) |
| *G01J 3/02* | (2006.01) |

(52) U.S. Cl.
CPC .............. *G01J 4/04* (2013.01); *G01J 3/0205* (2013.01); *G01J 3/10* (2013.01); *G01J 3/447* (2013.01)

(58) Field of Classification Search
CPC ........................................................ G01J 4/04
USPC ......................................................... 356/326
See application file for complete search history.

(56) References Cited

U.S. PATENT DOCUMENTS

| | | | |
|---|---|---|---|
| 6,104,488 A | 8/2000 | Levan | |
| 7,345,767 B2 | 3/2008 | Liphwat | |
| 8,169,611 B2 | 5/2012 | Herzinger | |
| 2003/0071996 A1* | 4/2003 | Wang | G01B 11/00 356/369 |
| 2005/0018189 A1* | 1/2005 | Hampton | G01J 4/04 356/369 |
| 2009/0309049 A1* | 12/2009 | Van Dijk | G01J 3/02 250/578.1 |
| 2013/0320223 A1* | 12/2013 | Quintel | G01J 3/10 250/372 |

OTHER PUBLICATIONS

"A New Spectrometer Using Multiple Gratings with a Two-Dimensional Charge-Coupled Diode Array," Hanetal, Rev. of Sef. Inst., vol. 74, No. 6, Jun. 2003.

\* cited by examiner

*Primary Examiner* — Tarifur R Chowdhury
*Assistant Examiner* — Omar Nixon
(74) *Attorney, Agent, or Firm* — James D. Welch

(57) ABSTRACT

Application of detectors of electromagnetic radiation and systems for enabling the optimization thereof for application over various specific wavelength ranges, involving functional combinations of gratings and/or combination dichroic beam splitter-prisms, which themselves can be optimized as regards wavelength dispersion characteristics.

30 Claims, 4 Drawing Sheets

ENHANCED DETECTOR OPERATION MADE POSSIBLE BY APPLICATION OF A FUNCTIONAL PLURALITY OF GRATINGS AND COMBINATION DICHROIC BEAM SPLITTER-PRISMS

This Application Claim Benefit of Provisional Application Ser. No. 62/124,428, filed Dec. 18, 2014.

TECHNICAL FIELD

The present invention relates to the application of detectors of electromagnetic radiation and systems for enabling the optimization thereof for application over various specific wavelength ranges, involving functional combinations of gratings and/or combination dichroic beam splitter-prisms, which themselves can be optimized as regards wavelength dispersion characteristics.

BACKGROUND

It is well known to apply detectors of electromagnetic radiation in, for instance, ellipsometry. And it is known to use beam splitters to direct portions of beams into different detectors which can be optimized to respond to different wavelength ranges. A Patent to Herzinger et al. U.S. Pat. No. 8,169,611, for instance shows such an arrangement in FIG. 1a thereof, reproduced as FIG. 6 herein for easy reference). Many other references showing similar application of beam splitters in a similar manner exist. Also known are monochromater systems that utilizes a sequence of gratings with which a beam of spectroscopic electromagnetic radiation sequentially interacts to select a desired wavelength. FIG. 4 herein, (which is FIG. 9 in a Patent to Liphardt et al. U.S. Pat. No. 7,345,762), is included herein for easy reference, as it shows one example that shows such an arrangement. FIG. 5 herein, (which is FIG. 2 in said U.S. Pat. No. 7,345,762), is also included herein to demonstrate a dual grating spectrometer that enhances resolution of produced wavelengths, and finds application in ellipsometer or polarimeter systems.

Another known Patent is U.S. Pat. No. 6,104,488 to LeVan. This Patent is focused on providing high single grating efficiency, with different orders of wavelengths being produced thereby detected by a single detector.

An article titled "A New Spectrometer Using Multiple Gratings With A Two-Dimensional Charge-Coupled Diode Array Detector", Review of Scientific Instruments, Vol. 74, No. 6, June 2003, describes a special grating that consists of three laterally stacked sub-gratings to generate three wavelength ranges.

It is noted that the identified prior art is primarily focused on production of wavelength ranges.

Even in view of the known prior art there remains need for additional systems directed to optimizing application of a plurality of detectors and/or wavelength dispersing elements which are arranged sequentially, and wherein each follow-on wavelength dispersing element receives a reflected altered spectral content reflected beam of electromagnetic radiation from a preceding wavelength dispersing element, and wherein each wavelength dispersing element produces at least one + or − spectrum of dispersed wavelengths which are directed toward a related detector.

DISCLOSURE OF THE INVENTION

The present invention is a system for producing a plurality of separate wavelength ranges from a spectroscopic beam incident thereupon, said system comprising a sequence of at least two elements, each thereof being selected from the group consisting of:

a grating which when presented with an incident spectroscopic beam of electromagnetic radiation produces a spectrum of diffracted dispersed wavelengths and simultaneous therewith an altered spectral content reflected beam of electromagnetic radiation;

a combination dichroic beam splitter-prism which when presented with a spectroscopic beam of electromagnetic radiation produces a spectrum of dispersed wavelengths that transmit through and exit from said prism, and simultaneous therewith an altered spectral content reflected beam of electromagnetic radiation.

In use a spectroscopic beam of electromagnetic radiation is caused to impinge onto a first selected element such that a spectrum of dispersed wavelengths is produced and directed toward a first detector, simultaneous with production of a reflected altered spectral content reflected beam of electromagnetic radiation, at least some of which is directed to impinge on a second selected element which likewise produces a spectrum of dispersed wavelengths, which are directed toward a second detector.

A preferred approach provides that the spectrum of dispersed diffracted wavelengths produced by said grating is a + or − order spectrum. And it is noted that the altered spectral content reflected beam of electromagnetic radiation is typically selected to be a zero order beam that reflects from a grating, or a beam that reflects from a dichroic beam splitter in a combination dichroic beam splitter-prism combination.

The reflected altered spectral content reflected beam of electromagnetic radiation can be directed to impinge on a beam splitter that directs at least some of said beam onto a third selected element which produces a spectrum of dispersed wavelengths that are directed into a third detector, while continuing to direct at least some of said altered spectral content beam toward said second selected element which continues to direct the limited range spectrum of dispersed wavelengths produced thereby toward said second detector.

Said system can comprise at least one selection from the group consisting of:

at least one of said first and second selected elements is/are designed to optimally structure the range of wavelengths exiting therefrom;

at least one of said first and second detectors is/are designed to optimally detect the range of wavelengths input thereinto by said first and second selected elements respectively;

is functionally enabled.

The system can further comprise more than two selected elements selected from the selection group, and in which the reflected electromagnetic beam produced by the second selected element is directed toward at least one selection from the group consisting of:

a dichroic beam splitter and then therefrom impinge onto a third selected element;

directly impinge onto a third selected element;

at least one reflector and then a dichroic beam splitter and then therefrom impinge onto a third selected element; and at least one reflector and then impinge onto a third selected element.

The third selected element can, upon receiving said reflected beam of electromagnetic radiation, produce a spectrum of dispersed wavelengths which are directed toward a third detector.

The at least one selection from the group consisting of:
said third selected element is designed to optimally structure the range of wavelengths exiting therefrom;
said third detector is designed to optimally detect the range of wavelengths input thereinto by said first and second selected elements respectively;
is enabled.
(Note, the terminology "optimally" refers generally to tailoring a wavelength range and/or detector to meet specified criteria in a specified scenario. For instance, it might be desired to produce and monitor visual, or IR wavelengths. Specific grating design, Prism materials and coatings and detector types would be different for the different wavelength ranges).

A forth element can also be selected from the indicated selection group, and a the reflected electromagnetic beam produced by the third selected element, or which exits a present dichroic beam splitter associated with said second selected element, be directed toward at least one selection from the group consisting of:
a dichroic beam splitter and then therefrom impinge onto a forth selected element;
directly impinge onto a forth selected element;
at least one reflector and then a dichroic beam splitter and then therefrom impinge onto a forth selected element; and
at least one reflector and then impinge onto a forth selected element.

Said forth selected element, upon receiving said reflected beam of electromagnetic radiation can then produce a spectrum of dispersed wavelengths which are directed toward a forth detector.

At least one selection from the group consisting of:
said forth selected element is designed to optimally structure the range of wavelengths exiting therefrom;
said forth detector is designed to optimally detect the range of wavelengths input thereinto by said first and second selected elements respectively;
is enabled.

The system can specifically comprise a source of beam of spectroscopic electromagnetic radiation that is caused to imping onto a grating or a combination dichroic beam splitter-prism which produces said spectrum of diffracted dispersed wavelengths, which spectrum is directed to enter a detector; and simultaneously produce said altered spectral content reflected beam of electromagnetic radiation which is directed to interact with a dichroic beam splitter that causes said altered spectral content reflected beam of electromagnetic radiation to split into two beams, both of which are directed to separate selections from the group consisting of:
a grating which when presented with an incident spectroscopic beam of electromagnetic radiation produces a spectrum of diffracted dispersed wavelengths and simultaneous therewith an altered spectral content reflected beam of electromagnetic radiation;
a combination dichroic beam splitter-prism which when presented with a spectroscopic beam of electromagnetic radiation produces a spectrum of wavelengths that transmit through and exit from said prism, and simultaneous therewith an altered spectral content reflected beam of electromagnetic radiation;
such that the spectrum of dispersed wavelengths that exit from a present grating or combination dichroic beam splitter-prism are each caused to enter separate detectors.

The system can provide that the spectroscopic beam of electromagnetic radiation which is caused to impinge onto a first selected element such that a spectrum of dispersed wavelengths is produced and directed toward a first detector, simultaneous with production of an altered spectral content reflected beam of electromagnetic radiation which is directed to impinge on a second selected element which likewise produces a spectrum of dispersed wavelengths which are directed toward a second detector, is the output beam of an ellipsometer or polarimeter which exits the analyzer thereof.

Said system can specifically comprise a source of beam of spectroscopic electromagnetic radiation that is caused to direct a beam of electromagnetic radiation at a sequence of elements comprising:
a first grating and first and first detector, wherein the reflected beam exiting said first grating is a zero order beam and is directed to a second grating and second detector.

Said system can specifically comprise a source of beam of spectroscopic electromagnetic radiation that is caused to direct a beam of electromagnetic radiation at a sequence of elements comprising:
a first grating and first detector, wherein the reflected beam exiting said first grating is a zero order beam and is directed to a first combination dichroic beam splitter-prism and second detector.

Said system can specifically comprise a source of beam of spectroscopic electromagnetic radiation that is caused to direct a beam of electromagnetic radiation at a sequence of elements comprising:
a dichroic beam splitter which sends first and second ranges of dispersed wavelengths, which are substantially above and below a certain wavelength, respectively, each to a selection from the group consisting of:
a first grating and first detector, wherein the reflected beam exiting said first grating is a zero order beam and is directed to a second grating and second detector; and
a first grating and first detector, wherein the reflected beam exiting said first grating is a zero order beam and is directed to a first dichroic beam splitter-prism combination and second detector.

Said system can specifically comprise a source of beam of spectroscopic electromagnetic radiation that is caused to direct a beam of electromagnetic radiation at a sequence of elements comprising:
a first combination dichroic beam splitter-prism and first detector, and wherein the reflected beam reflecting from said first combination dichroic beam splitter-prism is directed to a first grating and second detector.

Said system can specifically comprise a source of beam of spectroscopic electromagnetic radiation that is caused to direct a beam of electromagnetic radiation at a sequence of elements comprising:
a first grating and first detector, wherein the reflected beam produced by said first grating is a zero order beam and is directed to a second grating and second detector, and in which the reflected beam produced by said second grating is a zero order beam directed to a third grating and third detector.

Said system can specifically comprise a source of beam of spectroscopic electromagnetic radiation that is caused to direct a beam of electromagnetic radiation at a sequence of elements comprising:
- a first grating and first detector, wherein the reflected beam produced by said first grating is a zero order beam and is directed to a first combination dichroic beam splitter-prism and second detector, and in which the reflected beam reflected from said first combination dichroic beam splitter-prism is directed to a third grating and third detector via a dichroic beam splitter.

Said system can specifically comprise a source of beam of spectroscopic electromagnetic radiation that is caused to direct a beam of electromagnetic radiation at a sequence of elements comprising:
- a first grating and first detector, wherein the reflected beam produced by said first grating is a zero order beam and is directed to a second grating and second detector, and in which the reflected beam produced by said second grating is a zero order beam and is directed to a first dichroic beam splitter-prism combination and third detector.

Said system can specifically comprise a source of beam of spectroscopic electromagnetic radiation that is caused to direct a beam of electromagnetic radiation at a sequence of elements comprising:
- a first grating and first detector, wherein the reflected beam produced by said first grating is a zero order beam and is directed to a first combination dichroic beam splitter-prism and second detector, and in which the reflected beam reflected from said first combination dichroic beam splitter-prism is directed to a second dichroic beam splitter-prism combination and third detector via a beam splitter.

Said system can specifically comprise a source of beam of spectroscopic electromagnetic radiation that is caused to direct a beam of electromagnetic radiation at a sequence of elements comprising:
- a first combination dichroic beam splitter-prism and first detector, wherein the reflected beam reflected by said first combination dichroic beam splitter-prism is directed to a second grating and second detector, and in which the reflected beam produced by said second grating is a zero order beam and is directed to a third grating and third detector.

Said system can specifically comprise a source of beam of spectroscopic electromagnetic radiation that is caused to direct a beam of electromagnetic radiation at a sequence of elements comprising:
- a first combination dichroic beam splitter-prism and first detector, wherein the reflected beam reflected from said first combination dichroic beam splitter-prism is directed to a second dichroic beam splitter-prism combination and second detector, and in which the reflected beam reflected from said second combination dichroic beam splitter-prism is directed to a third grating and third detector via a dichroic beam splitter.

Said system can specifically comprise a source of beam of spectroscopic electromagnetic radiation that is caused to direct a beam of electromagnetic radiation at a sequence of elements comprising:
- a first combination dichroic beam splitter-prism and first detector, wherein the reflected beam reflected from said first combination dichroic beam splitter-prism is directed to a first grating and second detector, and in which the reflected beam produced by said second grating is a zero order beam and is directed to a second combination dichroic beam splitter-prism and third detector.

Said system can specifically comprise a source of beam of spectroscopic electromagnetic radiation that is caused to direct a beam of electromagnetic radiation at a sequence of elements comprising:
- a first combination dichroic beam splitter-prism and first detector, wherein the reflected beam reflected from said first combination dichroic beam splitter-prism is directed to a second combination dichroic beam splitter-prism and second detector, and in which the reflected beam reflected from said combination second dichroic beam splitter-prism is directed to a third combination dichroic beam splitter-prism and third detector via a beam splitter.

A method of enhancing detector operation can comprise the steps of:
a) providing a system for producing a plurality of separate wavelength ranges from a spectroscopic beam incident thereupon, said system comprising a sequence of at least two elements, each thereof being selected from the group consisting of:
- a grating which when presented with an incident spectroscopic beam of electromagnetic radiation produces a spectrum of diffracted dispersed wavelengths and simultaneous therewith an altered spectral content reflected beam of electromagnetic radiation;
- a combination dichroic beam splitter-prism which when presented with a spectroscopic beam of electromagnetic radiation produces a spectrum of dispersed wavelengths that transmit through and exit from said prism, and simultaneous therewith an altered spectral content reflected beam of electromagnetic radiation;

such that in use a spectroscopic beam of electromagnetic radiation is caused to impinge onto a first selected element such that a spectrum of dispersed wavelengths is produced and directed toward a first detector, simultaneous with production of a reflected altered spectral content reflected beam of electromagnetic radiation which is directed to impinge on a second selected element which likewise produces a spectrum of dispersed wavelengths which are directed toward a second detector.

Said Method continues with:
b) causing a spectroscopic beam of electromagnetic radiation to impinge onto a first selected element such that a spectrum of dispersed wavelengths is produced and directed toward a first detector, simultaneous with production of a reflected altered spectral content reflected beam of electromagnetic radiation which is directed to impinge on a second selected element which likewise produces a spectrum of dispersed wavelengths which are directed toward a second detector.

Said method can further comprise providing a beam splitter between said first and second selected elements which each produce a spectrum of dispersed wavelengths which are directed toward a second detector; and
b) causing the reflected altered spectral content reflected beam of electromagnetic radiation which is directed to impinge on a beam splitter so that it directs at least some of said beam into onto a third selected element which produces a spectrum of dispersed wavelengths and directs it into a third detector, while also directing at least some of said beam toward said second selected element which continues to direct the spectrum of dispersed wavelengths produced thereby toward said second detector.

Said method preferably provides that the spectrum of dispersed diffracted wavelengths produced by a grating is a + or − order spectrum.

(It is noted that the altered spectral content reflected beam of electromagnetic radiation is typically selected to be a zero order beam that reflects from a grating, and a beam that reflects from a dichroic beam splitter in a combination dichroic beam splitter-prism combination).

The present invention will be better understood by reference to the Detailed Description of this Specification in conjunction with the Drawings.

BRIEF DESCRIPTION OF THE DRAWINGS

FIG. 3a' shows the situation wherein a Reflected (RB) beam is reflected from dichroic beam splitter-prism (DBS-PR) combination at a surface thereof on which is present a Coating, to give it the Dichroic property. Note that a spectrum of at least a + or − order spectrum exits the Prism (P).

DETAILED DESCRIPTION

Figure 1:
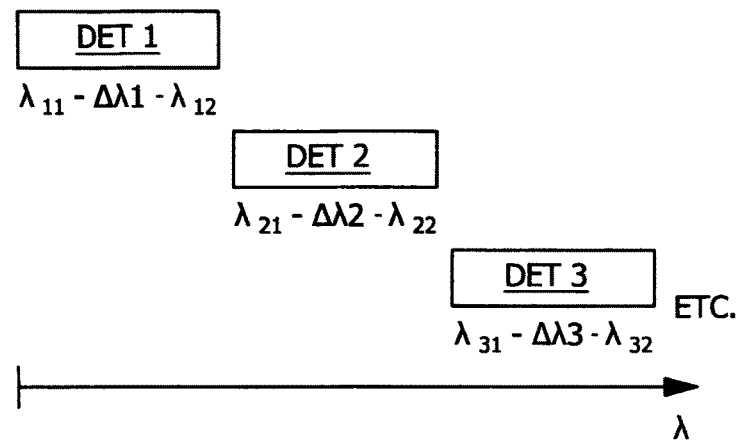
FIG. 1 demonstrates a number of wavelength ranges in which various multi-channel detectors (DET1) (DET2) (DET3) are designed to handle optimally.

Turning now to FIG. 1, there are demonstrated a number of wavelength ranges in which various multi-channel detectors (DET1) (DET2) (DET3) are designed to handle optimally. Many additional wavelength ranges could be shown similarly as well, such as a (Δλ 4) as shown in FIG. 2.

Figure 2:
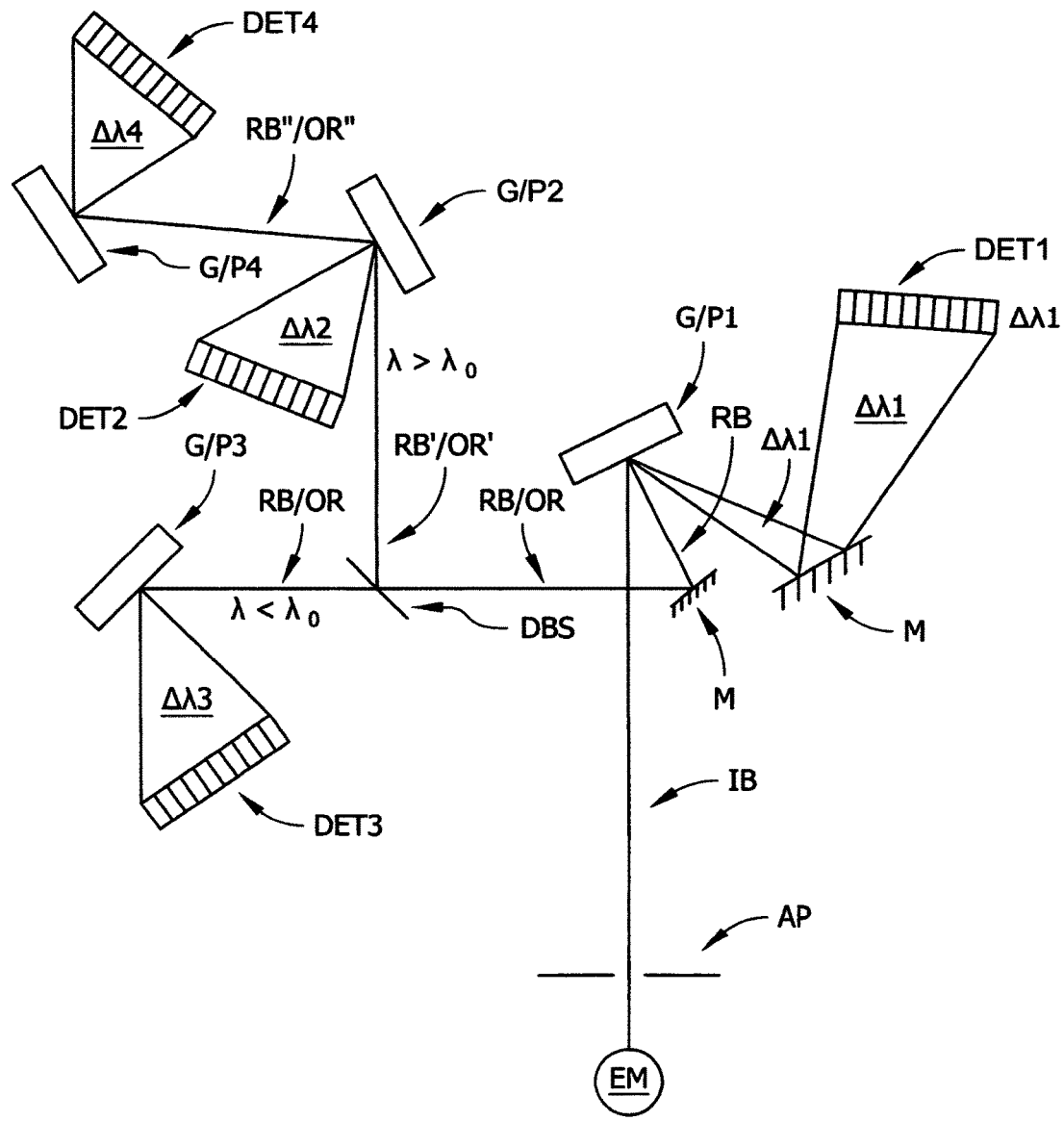
FIG. 2 shows some present invention combinations of multiple Gratings (G) and/or Dichroic Beam Splitter-Prism Combinations (DBSP), (generically represented as (G/P)), as examples that each produce at least one + or − order spectrum of wavelengths as well as a relatively more energetic Reflected Beam, (eg. Zero Order (ZO) in the case of a Grating), beam of electromagnetic radiation, which is directed to a follow-on Grating (G).

FIG. 2 shows combinations multiple Gratings (G) and/or Dichroic Beam Splitter-Prism Combinations (DBSP), (represented G/P"_" in FIG. 2), that each produce at least one + or − order spectrum (Δ) of wavelengths, as well as an altered spectral content Reflected (RB/OR) beam of electromagnetic radiation, (eg. a Zero Order (OR) beam as in the case of a Grating (G) or a functionally similar Reflected Beam (RB) in the case of a Dichroic Beam Splitter-Prism Combinations (DBSP). See Reflected Beam (RB) in FIG. 3a' as regards a combination dichroic beam splitter-prism (DBSP) and Zero Order (OR) Beam in FIG. 3a.

(Note, the terminology Zero Order (ZO) is not correct in a critical sense where a Dichroic Beam Splitter-Prism Combinations (DBSP), rather than a Grating (G) is applied, even though the results provided are functionally similar). FIG. 2 is a relevant example of a Present Invention System wherein a Source (EM) of a Beam of electromagnetic radiation (IB) is shown to provide electromagnetic radiation through an Aperture (AP), and impinge on (G/P1). Exiting (G/P1) is a First Range of a + or −, typically first Order spectrum of wavelengths (λ) which proceed, via reflection from a Mirror (M) as shown to Detector (DET1). Also shown is Reflected beam (RB) which reflects from another Mirror (M) and encounters a Dichroic Beam Splitter (DBS), which (DBS) directs a first amount of the entering beam to (G/P3) which disperses it into a range of wavelengths (λ) which are directed into Detector (DET3). A second amount of the Beam entering the (DBS) exits toward (G/P2) which provides a dispersed ranger of wavelengths (λ) that are directed into Detector (DET2), and also directs a Reflected Beam (RB"/OR") to (G/P4) which provides a dispersed range of wavelengths (Δλ4) to Detector (DET4).

Figure 3A:
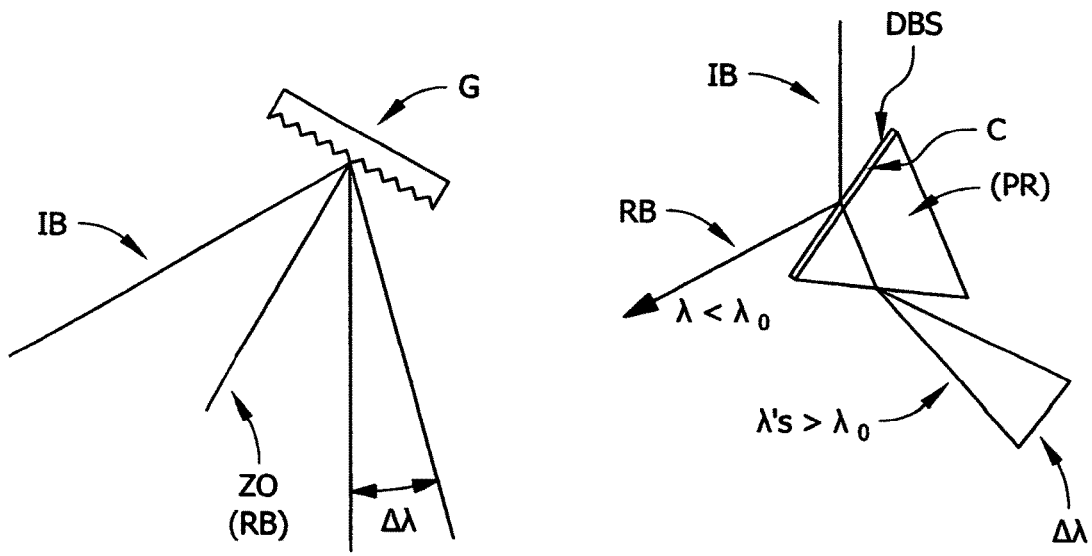
FIG. 3a shows a grating (G) that reflects an incoming beam (IB) of electromagnetism, and provides a spectrum of wavelengths (λ) in an order thereof, (eg. the first + Order), along with a Zero Order (ZO).

FIG. 3a demonstrates a Grating (G) wherein an Input Beam (IB) of electromagnetic radiation is impinged thereonto, with the result that at least one +/− Order Spectrum of wavelengths is produced along with a Zero Order (ZO) beam.

FIG. 3a' shows the situation wherein a Reflected (RB) beam is reflected from Dichroic Beam Splitter-Prism (DBS-PR) combination at a surface thereof on which is present a Coating, to give it the Dichroic property. Note that a spectrum of at least a + or − order spectrum exits the Prism (P). A coating (C) is indicated as present on the surface onto which the Input Beam impinges, and serves to form the Dichroic Beam Splitter (DBS). For insight, Dichroic refers to different properties, eg. reflection/transmission of electromagnetic radiation, based on wavelength.

It is to be understood that the designations of (G/P_) in FIG. 2 is to be interpreted as being either of the systems in FIGS. 3a and 3a'.

Figure 4:
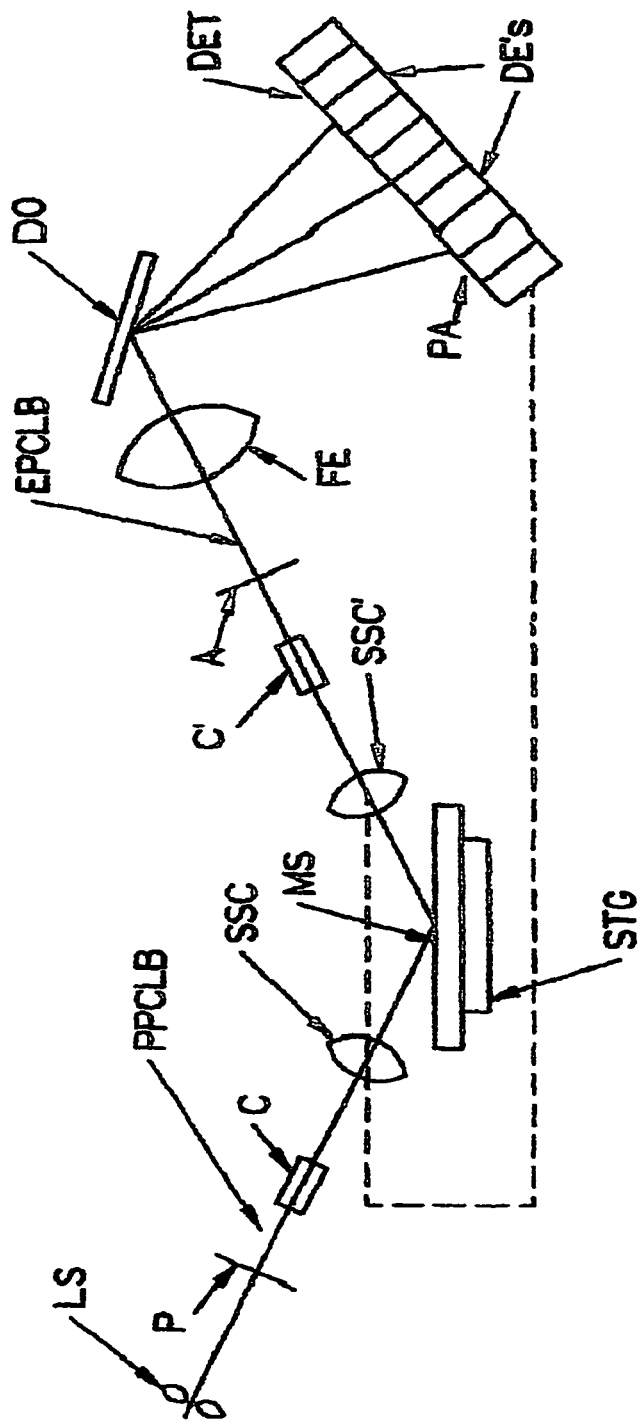
FIG. 4 demonstrates an ellipsometer system, in which the present invention finds very relevant application.

FIG. 4, (which is FIG. 2 taken from U.S. Pat. No. 7,345,762 to liphardt et al.), is included to demonstrate an ellipsometer system, in which ellipsometer and polarimeter and the like systems the present invention finds very relevant application. When so applied the beam exiting the ellipsometer polarization state analyzer, (ie. (EPCLB) in said FIG. 4), is beneficially considered as being the beam (IB) shown in accompanying FIG. 2. Roughly, Grating (G1) in FIG. 2 corresponds to Dispersive Element (ie. Grating), (DO) in said FIG. 4. Note that FIG. 4 shows an ellipsometer Source (LS) which provides an ellipsometer beam (PPCLB) which has been polarized by interaction with the shown Polarizer (P). Said beam (PPCLB) is then caused to interact with a shown Sample (MS), which is indicated can be a focused beam at that point. A beam reflected from said Sample (MS) can be recollimated, and then pass through an Analyzer (A) and emerge as beam (EPCLB), before being focused by (FE) onto a Dispersive Element, (eg. a Grating) (DO), which (DO) serves to disperse wavelengths into a Multi-element (DE'S) Detector (PA). One or two Compensators (C) can also be present as shown in the Polarization State Generator or Analyzer or the system associated with the Polarizer and Analyzer respectively. Again, for correspondence, Dispersive Element (DO) is roughly equivalent to Grating (G1) in FIG. 2. Also shown is indication that the Focusing (SSC) and Recollimating (SSC') lenses can be controlled as to position to optimize intended effects.

Figure 5:
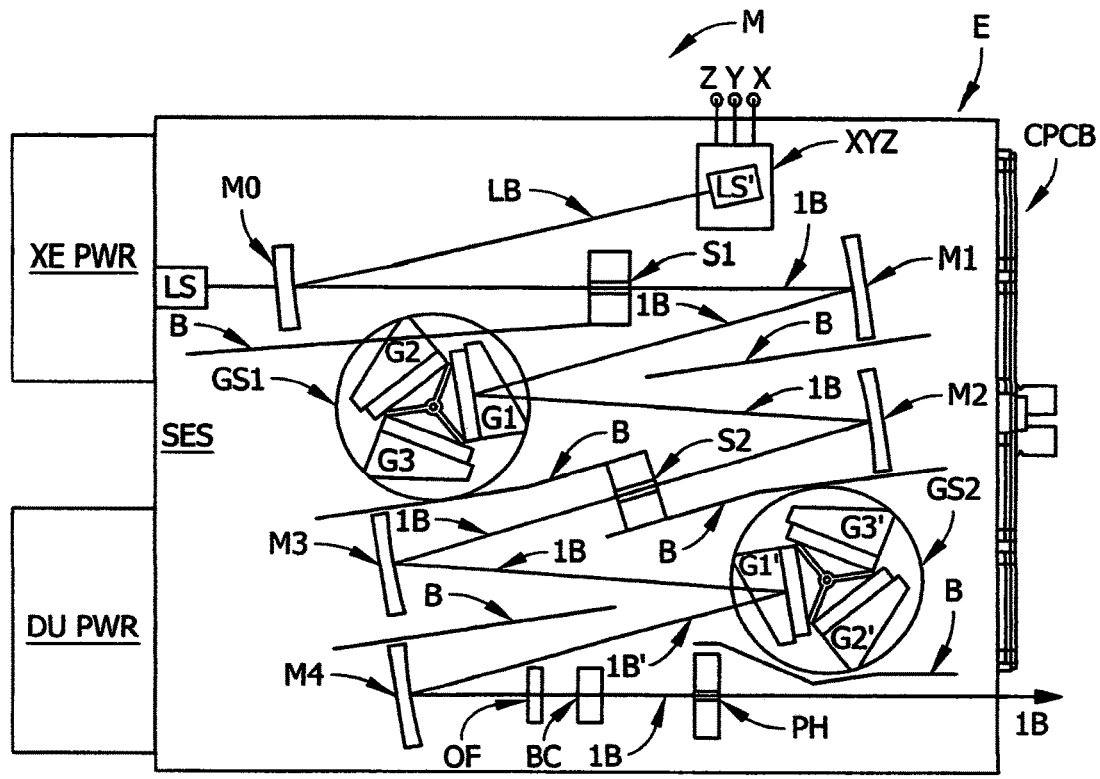
FIG. 5 shows the use of sequential follow-on Gratings which electromagnetic radiation sequentially caused to encounter.
Figure 6:
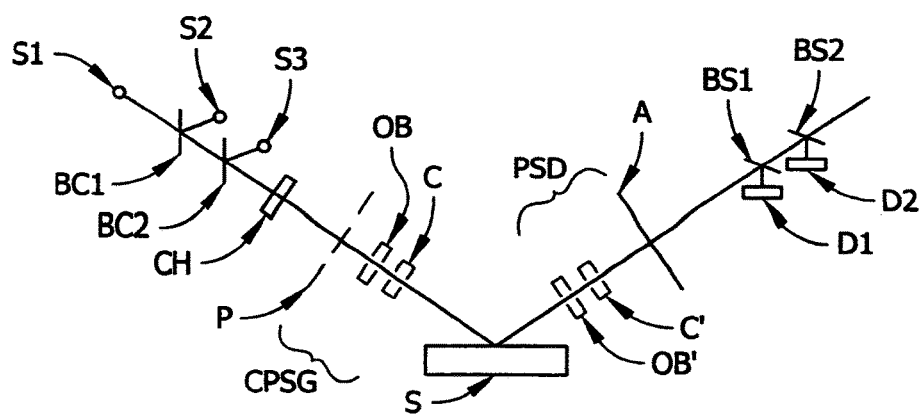
FIG. 6 shows the use of beam splitters to direct portions of beams into different detectors which can be optimized to respond to different wavelength ranges.

FIG. 5, (from FIG. 9 in U.S. Pat. No. 7,345,762), is included to show the use of sequential follow-on Gratings (eg. G1 and G1') to arrive at a desired wavelength in a spectrometer system. FIG. 6, (taken from FIG. 1a in U.S. Pat. No. 8,169,611), is included to show the use of beam splitters (B1, and B2) to direct portions of beams into different detectors (D1 and D2) which can be optimized to respond to different wavelength ranges. See U.S. Pat. Nos. 7,345,762 and 8,169,611 for more clarification. Said Patents however, do not suggest the present invention directing a Reflected altered spectral content Beam to follow-on beam dispersing elements.

The +/− orders shown in the Drawings can be described generally as being wavelength ranges that are produced when a grating is presented with an incident spectroscopic beam of electromagnetic radiation and in response produces a spectrum of diffracted dispersed wavelengths, and simultaneous with an altered spectral content reflected beam of electromagnetic radiation, typically a Zero-Order beam.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for producing, and detecting in multi-channel detectors, a plurality of separate wavelength ranges from a spectroscopic beam incident thereupon, said system comprising a sequence of at least two elements, each thereof being selected from the group consisting of:
   a grating which when presented with an incident spectroscopic beam of electromagnetic radiation produces a spectrum of diffracted dispersed wavelengths and simultaneous therewith an altered spectral content reflected beam of electromagnetic radiation; and
   a combination dichroic beam splitter-prism which when presented with a spectroscopic beam of electromagnetic radiation produces a spectrum of dispersed wavelengths that transmit through and exit from said prism, and simultaneous therewith an altered spectral content reflected beam of electromagnetic radiation;
such that in use a spectroscopic beam of electromagnetic radiation is caused to impinge onto a first selected element such that a spectrum of dispersed wavelengths is produced which dispersed wavelengths are, without the requirement of additional processing, directed toward a first multi-channel detector, simultaneous with production of a reflected altered spectral content reflected beam of electromagnetic radiation, at least some of which is directed to impinge on a second selected element which likewise produces a spectrum of dispersed wavelengths, which dispersed wavelengths are, without the requirement of additional processing, directed toward a second multi-channel detector.

2. A system as in claim 1, in which the reflected altered spectral content reflected beam of electromagnetic radiation is directed to impinge on a beam splitter that directs at least some of said beam onto a third selected element which produces a spectrum of dispersed wavelengths that are directed into a third multi-channel detector, while continuing to direct at least some of said altered spectral content beam toward said second selected element which continues to direct the limited range spectrum of dispersed wavelengths produced thereby toward said third multi-channel detector.

3. A system as in claim 1, in which at least one selection from the group consisting of:
   at least one of said first and second selected elements is/are designed to optimally structure the range of wavelengths exiting therefrom; and
   at least one of said first and second multi-channel detectors is/are designed to optimally detect the range of wavelengths input thereinto by said first and second selected elements respectively;
is functionally enabled.

4. A system as in claim 1 which further comprises more than two selected elements selected from the claim 1 group, and in which the reflected electromagnetic beam produced by the second selected element is directed toward at least one selection from the group consisting of:
   a dichroic beam splitter and then therefrom impinge onto a third selected element;
   directly impinge onto a third selected element;
   at least one reflector and then a dichroic beam splitter and then therefrom impinge onto a third selected element; and
   at least one reflector and then impinge onto a third selected element.

5. A system as in claim 4 in which the third selected element, upon receiving said reflected beam of electromagnetic radiation produces a spectrum of dispersed wavelengths which are directed toward a third multi-channel detector.

6. A system as in claim 5, in which at least one selection from the group consisting of:
   said third selected element is designed to optimally structure the range of wavelengths exiting therefrom; and
   said third multi-channel detector is designed to optimally detect the range of wavelengths input thereinto by said first and second selected elements respectively;
is enabled.

7. A system as in claim 4 in which a forth element is selected from the indicated claim 1 group and in which the reflected electromagnetic beam produced by the third selected element or which exits a present dichroic beam splitter associated with said second selected element, is directed toward at least one selection from the group consisting of:
   a dichroic beam splitter and then therefrom impinge onto a forth selected element;
   directly impinge onto a forth selected element;
   at least one reflector and then a dichroic beam splitter and then therefrom impinge onto a forth selected element; and
   at least one reflector and then impinge onto a forth selected element.

8. A system as in claim 7 in which the forth selected element, upon receiving said reflected beam of electromagnetic radiation produces a spectrum of dispersed wavelengths which are directed toward a forth multi-channel detector.

9. A system as in claim 8, in which at least one selection from the group consisting of:
   said forth selected element is designed to optimally structure the range of wavelengths exiting therefrom; and
   said forth multi-channel detector is designed to optimally detect the range of wavelengths input thereinto by said first and second selected elements respectively;
is enabled.

10. A system as in claim 1, which specifically comprises a source of beam of spectroscopic electromagnetic radiation that is caused to imping onto a grating or a combination dichroic beam splitter-prism which produces said spectrum of diffracted dispersed wavelengths, which spectrum is directed to enter a multi-channel detector; and simultaneously produces said altered spectral content reflected beam of electromagnetic radiation which is directed to interact with a dichroic beam splitter that causes said altered spectral content reflected beam of electromagnetic radiation to split into two beams, both of which are directed to separate selections from the group consisting of:
- a grating which when presented with an incident spectroscopic beam of electromagnetic radiation produces a spectrum of diffracted dispersed wavelengths and simultaneous therewith an altered spectral content reflected beam of electromagnetic radiation; and
- a combination dichroic beam splitter-prism which when presented with a spectroscopic beam of electromagnetic radiation produces a spectrum of wavelengths that transmit through and exit from said prism, and simultaneous therewith an altered spectral content reflected beam of electromagnetic radiation;

such that the spectrum of dispersed wavelengths that exit from a present grating or combination dichroic beam splitter-prism are each caused to enter separate multi-channel detectors.

11. A system as in claim 1 wherein the spectroscopic beam of electromagnetic radiation which is caused to impinge onto a first selected element such that a spectrum of dispersed wavelengths is produced and directed toward a first multi-channel detector, simultaneous with production of an altered spectral content reflected beam of electromagnetic radiation which is directed to impinge on a second selected element which likewise produces a spectrum of dispersed wavelengths which are directed toward a second multi-channel detector, is the output beam of an ellipsometer or polarimeter which exits the analyzer thereof.

12. A system as in claim 1, which specifically comprises a source of beam of spectroscopic electromagnetic radiation that is caused to direct a beam of electromagnetic radiation at a sequence of elements comprising:
- a first grating and first and first multi-channel detector, wherein the reflected beam exiting said first grating is a zero order beam and is directed to a second grating and second multi-channel detector.

13. A system as in claim 1, which specifically comprises a source of beam of spectroscopic electromagnetic radiation that is caused to direct a beam of electromagnetic radiation at a sequence of elements comprising:
- a first grating and first multi-channel detector, wherein the reflected beam exiting said first grating is a zero order beam and is directed to a first combination dichroic beam splitter-prism and second multi-channel detector.

14. A system as in claim 1, which specifically comprises a source of beam of spectroscopic electromagnetic radiation that is caused to direct a beam of electromagnetic radiation at a sequence of elements comprising:
- a dichroic beam splitter which sends first and second ranges of dispersed wavelengths, which are substantially above and below a certain wavelength, respectively, each to a selection from the group consisting of:
  - a first grating and first multi-channel detector, wherein the reflected beam exiting said first grating is a zero order beam and is directed to a second grating and second multi-channel detector; and
  - a first grating and first multi-channel detector, wherein the reflected beam exiting said first grating is a zero order beam and is directed to a first dichroic beam splitter-prism combination and second multi-channel detector.

15. A system as in claim 1, which specifically comprises a source of beam of spectroscopic electromagnetic radiation that is caused to direct a beam of electromagnetic radiation at a sequence of elements comprising:
- a first combination dichroic beam splitter-prism and first multi-channel detector, and wherein the reflected beam reflecting from said first combination dichroic beam splitter-prism is directed to a first grating and second multi-channel detector.

16. A system as in claim 1, which specifically comprises a source of beam of spectroscopic electromagnetic radiation that is caused to direct a beam of electromagnetic radiation at a sequence of elements comprising:
- a first grating and first multi-channel detector, wherein the reflected beam produced by said first grating is a zero order beam and is directed to a second grating and second multi-channel detector, and in which the reflected beam produced by said second grating is a zero order beam directed to a third grating and third multi-channel detector.

17. A system as in claim 1, which specifically comprises a source of beam of spectroscopic electromagnetic radiation that is caused to direct a beam of electromagnetic radiation at a sequence of elements comprising:
- a first grating and first multi-channel detector, wherein the reflected beam produced by said first grating is a zero order beam and is directed to a first combination dichroic beam splitter-prism and second multi-channel detector, and in which the reflected beam reflected from said first combination dichroic beam splitter-prism is directed to a third grating and third multi-channel detector via a dichroic beam splitter.

18. A system as in claim 1, which specifically comprises a source of beam of spectroscopic electromagnetic radiation that is caused to direct a beam of electromagnetic radiation at a sequence of elements comprising:
- a first grating and first multi-channel detector, wherein the reflected beam produced by said first grating is a zero order beam and is directed to a second grating and second multi-channel detector, and in which the reflected beam produced by said second grating is a zero order beam and is directed to a first dichroic beam splitter-prism combination and third multi-channel detector.

19. A system as in claim 1, which specifically comprises a source of beam of spectroscopic electromagnetic radiation that is caused to direct a beam of electromagnetic radiation at a sequence of elements comprising:
- a first grating and first multi-channel detector, wherein the reflected beam produced by said first grating is a zero order beam and is directed to a first combination dichroic beam splitter-prism and second multi-channel detector, and in which the reflected beam reflected from said first combination dichroic beam splitter-prism is directed to a second dichroic beam splitter-prism combination and third multi-channel detector via a beam splitter.

20. A system as in claim 1, which specifically comprises a source of beam of spectroscopic electromagnetic radiation that is caused to direct a beam of electromagnetic radiation at a sequence of elements comprising:
- a first combination dichroic beam splitter-prism and first multi-channel detector, wherein the reflected beam reflected by said first combination dichroic beam slitter-prism is directed to a second grating and second detector, and in which the reflected beam produced by said second grating is a zero order beam and is directed to a third grating and third multi-channel detector.

21. A system as in claim 1, which specifically comprises a source of beam of spectroscopic electromagnetic radiation that is caused to direct a beam of electromagnetic radiation at a sequence of elements comprising:

a first combination dichroic beam splitter-prism and first multi-channel detector, wherein the reflected beam reflected from said first combination dichroic beam splitter-prism is directed to a second dichroic beam splitter-prism combination and second multi-channel detector, and in which the reflected beam reflected from said second combination dichroic beam splitter-prism is directed to a third grating and third multi-channel detector via a dichroic beam splitter.

22. A system as in claim 1, which specifically comprises a source of beam of spectroscopic electromagnetic radiation that is caused to direct a beam of electromagnetic radiation at a sequence of elements comprising:
a first combination dichroic beam splitter-prism and first multi-channel detector, wherein the reflected beam reflected from said first combination dichroic beam splitter-prism is directed to a first grating and second multi-channel detector, and in which the reflected beam produced by said second grating is a zero order beam and is directed to a second combination dichroic beam splitter-prism and third multi-channel detector.

23. A system as in claim 1, which specifically comprises a source of beam of spectroscopic electromagnetic radiation that is caused to direct a beam of electromagnetic radiation at a sequence of elements comprising:
a first combination dichroic beam splitter-prism and first multi-channel detector, wherein the reflected beam reflected from said first combination dichroic beam splitter-prism is directed to a second combination dichroic beam splitter-prism and second multi-channel detector, and in which the reflected beam reflected from said combination second dichroic beam splitter-prism is directed to a third combination dichroic beam splitter-prism and third multi-channel detector via a beam splitter.

24. A system as in claim 1, wherein the spectrum of dispersed diffracted wavelengths produced by said grating is a + or − order spectrum.

25. A system as in claim 1, wherein the system further comprises a source of a spectroscopic beam of electromagnetic radiation, a polarizer, a stage for supporting a sample, and an analyzer, with which said polarizer, and a sample placed on said stage for supporting it, and said analyzer the spectroscopic beam of electromagnetic radiation from said source thereof interacts before entering the selected wavelength diffracting grating or the wavelength diffracting combination dichroic beam splitter-prism element, and which system is an ellipsometer or polarimeter.

26. A method of enhancing detector operation comprising the steps of:
a) providing a system for producing and detecting in multi-channel detectors, a plurality of separate wavelength ranges from a spectroscopic beam incident thereupon, said system comprising a sequence of at least two elements, each thereof being selected from the group consisting of:
a grating which when presented with an incident spectroscopic beam of electromagnetic radiation produces a spectrum of diffracted dispersed wavelengths and simultaneous therewith an altered spectral content reflected beam of electromagnetic radiation; and
a combination dichroic beam splitter-prism which when presented with a spectroscopic beam of electromagnetic radiation produces a spectrum of dispersed wavelengths that transmit through and exit from said prism, and simultaneous therewith an altered spectral content reflected beam of electromagnetic radiation;
such that in use a spectroscopic beam of electromagnetic radiation is caused to impinge onto a first selected element such that a spectrum of dispersed wavelengths is produced which dispersed wavelengths are, without the requirement of additional processing, directed toward a first multi-channel detector, simultaneous with production of a reflected altered spectral content reflected beam of electromagnetic radiation, at least some of which is directed to impinge on a second selected element which likewise produces a spectrum of dispersed wavelengths, which dispersed wavelengths are, without the requirement of additional processing, directed toward a second multi-channel detector;
b) causing a spectroscopic beam of electromagnetic radiation to impinge onto a first selected element such that a spectrum of dispersed wavelengths is produced and directed toward, and detected by a plurality of specific detector elements in a first multi-channel detector, simultaneous with production of a reflected altered spectral content reflected beam of electromagnetic radiation which is directed to impinge on a second selected element which likewise produces a spectrum of dispersed wavelengths which are directed toward, and detected by a plurality of channel detector elements in a second multi-channel detector.

27. A method as in claim 26 which further comprises providing a beam splitter between said first and second selected elements which each produce a spectrum of dispersed wavelengths which are directed toward a second multi-channel detector; and
b) causing the reflected altered spectral content reflected beam of electromagnetic radiation which is directed to impinge on a beam splitter so that it directs at least some of said beam into onto a third selected element which produces a spectrum of dispersed wavelengths and directs it into, and is detected by a plurality of channel detector elements in a third multi-channel detector, while also directing at least some of said beam toward said second selected element which continues to direct the spectrum of dispersed wavelengths produced thereby toward said multi-channel second detector.

28. A method as in claim 26, wherein the spectrum of dispersed diffracted wavelengths produced by said grating is a + or − order spectrum.

29. A method as in claim 26, wherein the step of providing a system further comprises providing a source of a spectroscopic beam of electromagnetic radiation, a polarizer, a stage for supporting a sample, and an analyzer, with which said polarizer, and a sample placed on said stage for supporting it, and said analyzer the spectroscopic beam of electromagnetic radiation from said source thereof interacts before entering the selected wavelength diffracting grating or the wavelength diffracting combination dichroic beam splitter-prism element, and which system is an ellipsometer or polarimeter.

30. A system for producing, and detecting in a multi-channel detector, a plurality of separate wavelength ranges from a spectroscopic beam incident thereupon, said system comprising a sequence of at least two selected elements, said at least two selected elements being, in either order:
a grating which when presented with an incident spectroscopic beam of electromagnetic radiation produces a spectrum of diffracted dispersed wavelengths and simultaneous therewith an altered spectral content reflected beam of electromagnetic radiation; and a combination dichroic beam splitter-prism which when presented with a spectroscopic beam of electromagnetic radiation produces a spectrum of dispersed wavelengths that transmit through and exit from said prism, and simultaneous therewith an altered spectral content reflected beam of electromagnetic radiation;

such that in use a spectroscopic beam of electromagnetic radiation is caused to impinge onto a first selected element such that a + or − order spectrum of dispersed wavelengths is produced and directed toward a first multi-channel detector, simultaneous with production of a reflected altered spectral content reflected beam of electromagnetic radiation, at least some of which is directed to impinge on the second selected element which likewise produces a spectrum of dispersed wavelengths, such that a + or − order spectrum of dispersed wavelengths is produced and directed toward a second multi-channel detector.

* * * * *